United States Patent
Goldberg et al.

(10) Patent No.: US 9,539,171 B2
(45) Date of Patent: Jan. 10, 2017

(54) APPARATUS FOR REDUCING PAIN DURING SKIN-PUNCTURING PROCEDURES

(75) Inventors: Steven Goldberg, Boca Raton, FL (US); David Schiff, Highland Park, NJ (US); Chris Evans, Brooklyn, NY (US); John Coleman, Philadelphia, PA (US)

(73) Assignee: BING INNOVATIONS, LLC, Boca Raton, FL (US)

( * ) Notice: Subject to any disclaimer, the term of this patent is extended or adjusted under 35 U.S.C. 154(b) by 865 days.

(21) Appl. No.: 13/259,408

(22) PCT Filed: Mar. 26, 2010

(86) PCT No.: PCT/US2010/028858
§ 371 (c)(1),
(2), (4) Date: Sep. 23, 2011

(87) PCT Pub. No.: WO2010/111611
PCT Pub. Date: Sep. 30, 2010

(65) Prior Publication Data
US 2012/0016292 A1 Jan. 19, 2012

Related U.S. Application Data

(63) Continuation of application No. PCT/US2009/066033, filed on Nov. 29, 2009.
(Continued)

(51) Int. Cl.
*A61B 17/20* (2006.01)
*A61H 23/02* (2006.01)
(Continued)

(52) U.S. Cl.
CPC .......... *A61H 23/0254* (2013.01); *A61H 7/005* (2013.01); *A61M 5/422* (2013.01);
(Continued)

(58) Field of Classification Search
CPC ................... A61M 2205/43; A61M 2205/581; A61M 2205/59; A61M 2205/26; A61H 2205/026; A61H 2201/0188
(Continued)

(56) References Cited

U.S. PATENT DOCUMENTS 1,485,963 A * 3/1924 Curry .......................... 433/116
2,247,258 A 6/1941 Shepard
(Continued)

FOREIGN PATENT DOCUMENTS

AU 2010229783 9/2015
CA 2580792 10/2013
(Continued)

OTHER PUBLICATIONS

For U.S. Appl. No. 13/225,782: restriction requirement dated Apr. 26, 2013 and response dated Jun. 26, 2013.
(Continued)

*Primary Examiner* — Edelmira Bosques
(74) *Attorney, Agent, or Firm* — Paul D. Bianco; Katharine Davis; Fleit Gibbons Gutman Bongini & Bianco PL

(57) ABSTRACT

An instrument, article and method are provided for minimizing pain during administration by injection of a liquid, such as, an anesthetic. The instrument has a forward end. A lightpipe mounted freely for vibration projects out of the forward end. The article, a single use tip, is composed of a tip sleeve removably mounted on the forward end of the instrument and a tip member removably mounted on the projecting lightpipe to vibrate a preselected injection site on a human or animal. The tip sleeve and tip member are covered by an elastic overmold that enables the tip member to vibrate freely with respect to the tip sleeve and light from the lightpipe to illuminate the injection site. A vibration unit
(Continued)

mounted in the instrument is coupled to the lightpipe. The method is carried out by imparting vibrations and illumination via the lightpipe to the tip member.

21 Claims, 15 Drawing Sheets

Related U.S. Application Data

(60) Provisional application No. 61/163,945, filed on Mar. 27, 2009.

(51) Int. Cl.
*A61H 7/00* (2006.01)
*A61M 5/42* (2006.01)
*A61H 13/00* (2006.01)

(52) U.S. Cl.
CPC ...... *A61H 13/00* (2013.01); *A61H 2201/0153* (2013.01); *A61H 2201/0188* (2013.01); *A61H 2201/1418* (2013.01); *A61H 2201/1688* (2013.01); *A61H 2203/03* (2013.01); *A61H 2205/026* (2013.01); *A61M 2205/43* (2013.01); *A61M 2205/581* (2013.01); *A61M 2205/59* (2013.01)

(58) Field of Classification Search
USPC ............................................. 604/22; 433/116
See application file for complete search history.

(56) References Cited

U.S. PATENT DOCUMENTS

| | | | |
|---|---|---|---|
| 2,258,857 A | 10/1941 | McCann | |
| 3,590,232 A | 6/1971 | Sadowski | |
| 3,620,209 A | 11/1971 | Kravitz | |
| 3,837,595 A | 9/1974 | Boone | |
| 4,091,805 A | 5/1978 | Clark | |
| 4,572,180 A | 2/1986 | Deenadayalu | |
| 4,593,973 A * | 6/1986 | Yoshida et al. | 385/126 |
| 4,785,796 A | 11/1988 | Mattson | |
| 4,867,141 A | 9/1989 | Nakada et al. | |
| 5,437,606 A | 8/1995 | Tsukamoto | |
| 5,542,845 A * | 8/1996 | Jenkins | 433/116 |
| 5,636,988 A | 6/1997 | Murayama | |
| 5,639,238 A | 6/1997 | Fishburne, Jr. | |
| 5,647,851 A | 7/1997 | Pokras | |
| 5,647,853 A | 7/1997 | Feldmann et al. | |
| 5,692,900 A | 12/1997 | Fischer | |
| 5,704,902 A | 1/1998 | Vandenbelt et al. | |
| 5,928,170 A | 7/1999 | Garrigan | |
| 5,938,435 A | 8/1999 | Raspino | |
| 5,989,022 A | 11/1999 | Yamamoto | |
| 6,030,210 A * | 2/2000 | Bianchetti | A61C 1/088 433/118 |
| 6,355,007 B1 | 3/2002 | Zuckerbrod | |
| 6,436,035 B1 | 8/2002 | Toth et al. | |
| 6,602,229 B2 | 8/2003 | Coss | |
| 6,923,762 B1 | 8/2005 | Creaghan, Jr. | |
| 7,244,266 B2 | 7/2007 | Garthe | |
| 7,981,071 B2 | 7/2011 | Goldberg | |
| 8,121,696 B2 | 2/2012 | Vallero | |
| 8,622,952 B2 | 1/2014 | Goldberg | |
| 8,668,664 B2 | 3/2014 | Goldberg | |
| 8,690,872 B2 | 4/2014 | Jayaraj | |
| 9,168,340 B2 | 10/2015 | Goldberg et al. | |
| 2002/0082564 A1 | 6/2002 | Pham | |
| 2003/0040714 A1 | 2/2003 | Coss | |
| 2003/0195644 A1 | 10/2003 | Borders et al. | |
| 2003/0225429 A1 | 12/2003 | Garthe et al. | |
| 2004/0077977 A1 | 4/2004 | Ella | |
| 2004/0254599 A1 | 12/2004 | Lipoma et al. | |
| 2005/0215952 A1 | 9/2005 | Brunel | |
| 2006/0106363 A1 | 5/2006 | Aravena et al. | |
| 2007/0088245 A1 | 4/2007 | Babaev et al. | |
| 2007/0145155 A1 | 6/2007 | Scarlatella | |
| 2007/0156179 A1 | 7/2007 | S.E. | |
| 2007/0167943 A1 | 7/2007 | Janssen et al. | |
| 2008/0086159 A1 | 4/2008 | Zweifler | |
| 2008/0255483 A1 | 10/2008 | Goldberg | |
| 2009/0047624 A1 | 2/2009 | Tsai | |
| 2009/0281464 A1 | 11/2009 | Cioanta et al. | |
| 2010/0125172 A1 | 5/2010 | Jayaraj | |
| 2010/0179457 A1 | 7/2010 | Blaine | |
| 2011/0054386 A1 | 3/2011 | Blaine et al. | |
| 2011/0270154 A1 | 11/2011 | Goldberg | |
| 2011/0319812 A1 | 12/2011 | Goldberg et al. | |
| 2012/0016292 A1 | 1/2012 | Goldberg et al. | |
| 2012/0029422 A1 | 2/2012 | Goldberg | |
| 2013/0095508 A1 | 4/2013 | Campitelli et al. | |
| 2013/0197317 A1 | 8/2013 | Daniel et al. | |
| 2013/0204202 A1 | 8/2013 | Trombly et al. | |
| 2013/0317314 A1 | 11/2013 | Lampson | |
| 2014/0055588 A1 | 2/2014 | Bangera et al. | |
| 2014/0121557 A1 | 5/2014 | Gannon | |
| 2014/0187870 A1 | 7/2014 | Weber | |
| 2014/0188095 A1 | 7/2014 | Weber | |
| 2014/0188128 A1 | 7/2014 | Weber | |
| 2014/0343432 A1 | 11/2014 | Humayun | |
| 2014/0371542 A1 | 12/2014 | Goldberg et al. | |
| 2014/0378940 A1 | 12/2014 | Lee | |
| 2015/0121557 A1 | 4/2015 | Pierce | |
| 2015/0134358 A1 | 5/2015 | Fisher | |
| 2015/0186702 A1 | 7/2015 | Pletcher et al. | |
| 2015/0216618 A1 | 8/2015 | Jayaraj | |
| 2015/0306286 A1 | 10/2015 | Ross et al. | |

FOREIGN PATENT DOCUMENTS

| | | |
|---|---|---|
| CN | 103826686 | 5/2014 |
| CN | ZL201080016524.X | 8/2014 |
| IL | 215355 | 9/2015 |
| JP | S6154832 | 4/1986 |
| JP | 548916 | 6/1993 |
| JP | 2002224183 | 8/2002 |
| JP | 2004129914 | 4/2004 |
| JP | 5549987 | 5/2014 |
| RU | 2011141339 | 5/2013 |
| RU | 2523203 | 5/2014 |
| WO | 03024513 A1 | 3/2003 |
| WO | 2004000196 A1 | 12/2003 |
| WO | 2006/034324 | 3/2006 |
| WO | 2008/042936 | 4/2008 |
| WO | 2010/110823 | 9/2010 |
| WO | 2010/111611 | 9/2010 |
| WO | 2013-036625 | 3/2014 |
| WO | 2015/081181 | 6/2015 |

OTHER PUBLICATIONS

For U.S. Appl. No. 13/179,674; office action dated Oct. 16, 2012; response dated Jan. 16, 2013; final office action dated Mar. 18, 2013; response dated Aug. 19, 2013.
Notice of Allowance for U.S. Appl. No. 13/253,572 dated Sep. 18, 2014 (related application).
Notice of Publication for HK Application No. 14108064.8 dated Sep. 26, 2014 (related application).
International Search Report, Written Opinion dated Nov. 30, 2012 for PCT/US12/53744.
International Preliminary Report on Patentability published Mar. 12, 2014 for PCT/US2012/053744.
Russian Decision on Granting for Russian application No. 2011141339/02 (061869) dated Mar. 19, 2014.
Japanese Office Action dated Jan. 7, 2014 for JP 2012-502291.
Decision to Grant for JP 2012-502291 dated Apr. 17, 2014.
Australian Patent Examination Report No. 1, dated May 5, 2014 for Patent application No. 2010229783, based on PCT/US10/028858.
Columbian Request for Technical Information dated Apr. 12, 2013.
Response to Columbian Request for Technical Information dated Jul. 15, 2013.

(56) References Cited

OTHER PUBLICATIONS

English translation of Japanese Office Action dated Jan. 7, 2014 for Japanese Patent Application No. JP2012-502291 filed on Sep. 20, 2012(related application).
European Search Report (ESR) for EP application No. 107569266.1—PCT/US2010028858 dated Aug. 20, 2013 (related application).
For U.S. Appl. No. 13/253,572 Office Actions dated Sep. 17, 2013; Feb. 6, 2014 Responses filed Dec. 17, 2103; May 5, 2014.
Response to Japanese Office Action dated Mar. 24, 2014 for Application No. JP2012521809 filed Sep. 20, 2012 (related application).
Office Action Summary dated Dec. 18, 2013 for MX/a/2011/010069 (related application).
International Search Report dated Dec 13, 2012 for International Patent Application No. PCT/ US2012/053943 filed Sep. 6, 2012 (related application).
International Preliminary Report of Patentability (IPRP) published Mar. 12, 2014 and Written Opinion (WO) published Mar. 6, 2014 for International Patent Application No. PCT/ US2012/053943 filed Sep. 6, 2012 (related application).
Russian Decision on Granting a Patent for Invention filed on Mar. 26, 2010 for Patent Application No. RU2011141339 filed May 10, 2013 (related application).
Office action dated Jan. 23, 2013 for Israeli application No. 215355.
Response to office action dated Jul. 2013 for Israeli application No. 215355.
Response to Mexican Office Action dated Feb. 4, 2014 for Mexican Application No. MX/a/2011/010069 (related application), with English translation.
Office Action dated Mar. 31, 2014 for MX/a/2011/010069 (related application).
First Office Action for Chinese Application No. 201080016524X (related application) with English translation from Chinese associate dated Nov. 20, 2012.
Response to First Chinese Office Action for Application No. 201080016524X (related application) dated Jun. 5, 2013.
Second Office Action for Chinese Application No. 201080016524X (related application) with English translation from Chinese associate dated Jul. 25, 2013.
Response to Second Chinese Office Action for Application No. 201080016524X (related application) dated Dec. 5, 2013.
Third Office Action for Chinese Application No. 201080016524X (related application) with English summary from Chinese associate dated Feb 27, 2014.
Official action from European Patent Office for EP 05303 150.1-1051 dated Nov. 16, 2011 (related application).
Response to official action from European Patent Office for EP 05 803 150.1 dated Mar. 26, 2012 (related application).
Second official action from European Patent Office for EP 05 803 150.1 dated Feb. 20, 2014 (related application).
Response filed with European Patent Office confirming applicant wishes to proceed for EP 05 303 150.1 dated Dec. 20, 2010 (related application).
Response to Mexican office ction dated Jun. 9, 2014 for Mexican Patent Application No. MX/A/2011/010069 (related application).
Response to the notice prior to examination for Israeli application No. 215355 filed May 12, 2014 (related application).
Notice Prior of Allowance dated Jul. 16, 2014 for Israeli application No. 21535 (related application).
Ronald Melzack and Patrick Wall, What is Gate Control Theory?, about.com Psychology, 1960.
Jul. 21. 2013 response to Jan. 23, 2013 Office Action for Israel Application No. 215355 (related application).
Response dated Mar. 12, 2014 to Office Action dated Sep. 6, 2013 for EP Application 10756926.1 (related application).
Response dated May 12, 2014 to third Office Action for Chinese Patent Application No. 201080016524.X (related application).
Supplemental Response filed Oct 10, 2013 for U.S. Appl. No. 13/179,674 (related application).
Office Action for U.S. Appl. No. 13/253,572 dated eptember 17, 2013 (related application).
Notice of Allowance dated Oct. 21, 2013 for U.S. Appl. No. 13/179,674 (related application).
Notice of Publication for China application No. 201280043253.6 dated Jun. 5, 2014 (related application).
For U.S. Appl. No. 13/225,782: notice of allowance dated Sep. 5, 2013.
Supplemental Response filed Oct. 10, 2013 for U.S. Appl. No. 13/179,674.
Supplementary European Search Report dated May 18, 2010 for Application No. EP05803150.
International Search Report published on Nov. 2, 2006, for PCT/US2005/33769, filed Sep. 19, 2005.
International Preliminary Report on Patentability published Mar. 20, 2007, for PCT/US2005/33769, filed Sep. 19, 2005.
Written Opinion published on Mar. 20, 2007, for PCT/US2005/33769, filed Sep. 19, 2005.
International Search Report dated Apr. 10, 2008, for PCT/US2007/80262, filed Oct. 3, 2007.
Written Opinion dated Apr. 10, 2008, for PCT/US2007/80262, filed Oct. 3, 2007.
International Preliminary Report on Patentability dated Apr. 7, 2009, for PCT/US2007/80262, filed Oct. 3, 2007.
International Search Report dated Jul. 16, 2010 for PCT/US2009/066033, published Sep. 30, 2010.
Written Opinion dated Jul. 15, 2010 for PCT/US2009/066033, published Sep. 30, 2010.
International Preliminary Report on Patentability dated Sep. 27, 2011 for PCT/US2009/066033, published Sep. 30, 2010.
International Search Report dated Dec. 21, 2010 for PCT/US10/28858 filed Mar. 26, 2010.
Written Opinion dated Dec. 20, 2010 for PCT/US10/28858 filed Mar. 26, 2010.
International Preliminary Report on Patentability dated Sep. 27, 2011 for PCT/US10/28858 filed Mar. 26, 2010.
Notice of Allowance dated Oct. 21; 2013 or U.S. Appl. No. 13/179,674 filed Jul. 11, 2011.
Office Action for U.S. Appl. No. 13/253,572 dated Sep. 17, 2013.
Taiwanese Office Action dated May 15, 2015 for Taiwanese Application No. 101132425.
Notice of Allowance dated Oct. 6, 2014 for Mexican Application No. MX/a/2011/010069.
Response Office Action filed Oct. 22, 2014 for Israeli Application No. 215355.
Notice of Allowance dated Oct. 2, 2014 for European Application No. 05 803 150.1-1651.
Notice Prior to Allowance dated Dec. 31, 2014 for Israeli Patent Application No. 215355.
Supplementary European Search Report dated Jan. 7, 2015 for European Application No. 12829549.
European Communication dated Jan. 23, 2015 for European Application No. 12829549.
Notice of Allowance dated Feb. 13, 2015 for U.S. Appl. No. 13/253,572.
International Search Report and Written Opinion of the International Searching Authority mailed Feb. 25, 2015 for PCT/US2014/67587.
Office Action dated Jul. 12, 2016 for U.S. Appl. No. 14/343,085.
Response to Final Office Action, dated Jul. 18, 2016 for U.S. Appl. No. 13/259,408.
Office Action dated Jun. 25, 2015 for U.S. Appl. No. 13/259,408.
Office Action dated Jun. 4, 2015 for Chinese Application No. 2012800432536.
Response filed Oct. 26, 2015 to Office Action dated Jun. 25, 2015 for U.S. Appl. No. 13/259,408.
Office Action dated Dec. 14, 2015 for U.S. Appl. No. 14/803,535.
Final Office Action dated Jan. 20, 2016 for U.S. Appl. No. 13/259,408.
Response filed Feb. 12, 2016 to Office Action dated Dec. 14, 2015 for U.S. Appl. No. 14/803,535.
Office Action dated Apr. 8, 2016 for Korean Patent Application No. 10-2011-7025440.

(56) References Cited

OTHER PUBLICATIONS

Response filed Jun. 8, 2016 for Office Action dated Apr. 8, 2016 for Korean Patent Application No. 10-2011-7025440.
Notice of Allowance dated Jun. 7, 2016 for U.S. Appl. No. 14/803,535.
International Preliminary Report on Patentability dated May 31, 2016 for PCT/US2014/067587.

* cited by examiner

APPARATUS FOR REDUCING PAIN DURING SKIN-PUNCTURING PROCEDURES

CROSS REFERENCE TO RELATED APPLICATIONS

This application is a U.S. National Stage Application of International Application No. PCT/US2010/028858 filed Mar. 26, 2010, which claims priority to International Application No. PCT/US2009/066033 filed Nov. 29, 2009 and U.S. Provisional Application No. 61/163,945 filed Mar. 27, 2009. The contents of each of the above-identified applications are incorporated herein by reference.

This application and the invention described herein is a continuation-part of PCT Application No. PCT/US09/66033 filed Nov. 29, 2009, which is a continuation-part of co-pending U.S. application Ser. No. 11/575,564 filed Mar. 19, 2007, both of which applications are here incorporated by reference in their entirety.

FIELD OF INVENTION

The invention relates to improvements to a method, article and apparatus for use in medical and dental procedures, and particularly to improvements to a method and apparatus in the form of a retractor vibrator and the article in the form of a disposable tip for reducing or minimizing pain during tissue or skin puncturing procedures, such as, administration by injection, into the gums, skin or other tissue of a patient, of a liquid, such as, and in particular, an anesthetic.

BACKGROUND OF THE INVENTION

As described in the former application, in the prior art, the normal procedure for reducing the pain when injecting a liquid, such as, an anesthetic, serum, vitamins, vaccine, or other medical or dental efficacious liquids is either to (a) place a very cold material against the skin or flesh of the patient at the injection site, (b) to apply a topical treatment to the skin or flesh at the injection site, which temporarily numbs the skin or flesh (c) rapidly manually massaging the skin or tissue at the injection site while performing the injection. Although these procedures have some effect, they are either cumbersome, require some time to complete or are of limited effect and do not reduce the pain to a satisfactory level. The invention described in the former application provided a unique and novel apparatus and method for reducing pain during skin puncturing procedures, particularly involving dentistry.

SUMMARY OF THE INVENTION

It is a general object of the present invention to provide improvements to the invention described in the former application, especially regarding the retractor vibrator and single use or disposable tip described. Through the use of the improvements described and claimed herein further disadvantages will be overcome when injecting an anesthetic, serum, vitamins, vaccine, or other medical or dental efficacious liquids. In particular, it is an object of the present invention to provide improvements to the apparatus, article and method previously described that can be easily and inexpensively utilized during a medical, veterinary or dental procedure to almost completely or substantially eliminate the pain attendant an injection as it punctures the skin or flesh of the patient.

In keeping with the objects of the present invention, the present invention comprises an improved method, an improved article in the form of a disposable tip and an improved hand-held apparatus, in its preferred form of a retractor vibrator, for vibrating a skin or tissue area, and preferably at least two skin or tissue areas or a circular skin or tissue area, immediately at an injection site simultaneously with injection by needle of a liquid, such as, an anesthesia, serum, vitamins, vaccine, or other medical or dental efficacious liquids, into the skin or tissue at the injection site in a more effective and sanitary manner. The region of interest for a dentist is the entire oral mucosa area and underlying bone whereas the region of interest for a medical doctor is the whole body and underlying bone. Such a typical injection procedure may involve an injection of Lidocaine into a patient's gum or other tissue during a dental procedure.

Accordingly it is an object of the invention to provide an improved instrument for minimizing pain during administration by injection of a liquid, such as, an anesthetic comprising a main body, a detachable tip (novel article) cantilever mounted on the main body in a unique manner to prevent re-use of the tip and a vibration unit mounted in the main body when initiated to cause the tip to vibrate in a unique and novel manner. The tip is vibrated and has a free end characterized by a bifurcation to form two spaced projections defining a space between them, whereby the spaced projections can be placed in proximity to a preselected injection site on a human or animal and the tissue at said preselected injection site vibrated while an injection is given, and then continuing the vibration to massage the tissue to dissipate the injected liquid into the tissue and prevent tissue distension and swelling of the tissue. Preferably, the subsequent vibration is effected with more pressure on the tissue by the person injecting to effect better massaging. The subsequent vibration is most effective if the pressure applied is sufficient to sound bone beneath the tissue. An ordinarily skilled-in-the-art dentist can sense when he is applying pressure to tissue, such as the gums, and his instrument is touching the gums is in good contact or effectively hitting on underlying bone. When bone contact is sensed, the pressure is maintained for 1 to 30 seconds. The area of the injection site is lighted by the instrument in a unique way. Also, improved performance is obtained by pulsing the vibrations according to a preferred duty cycle, such about one second on and about $\frac{1}{10}^{th}$ of a second off.

As a further improvement, the article in the form of a single use or disposable tip is comprised of a tip sleeve composed of a hard plastic such as polycarbonate, for mounting on the forward portion of an instrument by means of a detachable connection, such as a bayonet type, and a forked tip member, also composed of a hard plastic, which parts are held together in a slightly spaced relation by an overmold of rubber or a thermoplastic elastomer having a preselected durometer. The forked tip member has a cup formed in its base that is mounted on the vibrated lightpipe that projects out from the front of the instrument. A lens formed in the end of the cup shines light from the lightpipe onto the injection site. The prongs of the forked tip member extend forwardly and bend downwardly at an angle of approximately 55 degrees. An O-ring holds the lightpipe centered in the forward part of the instrument while allowing the lightpipe to vibrate freely.

As further objects of the invention an improved instrument as above can be arranged wherein the detachable tip includes a surface to act as a retractor, a control switch can be provided on the main body for on/off control of the vibration unit. Also, the tip can include an element that coacts with the improved instrument so that when placed on the improved instrument, the element activates a switch or contacts to turn the improved instrument on, and when the tip is removed, the removal action causes the element to fracture and break off so that reuse of the tip is impossible. As in the previous instrument, the improved instrument can include a music player in the main body for playing music through a speaker. Further the main body can include rechargeable batteries as a power source to drive the vibration unit. Still further a light source is provided on the main body directed toward the space defined between the spaced projections to light the area being injected to provide better visibility.

Also, another object of the invention includes a method comprising the steps of vibrating tissue of a human or animal in a unique manner that maintains the vibration fresh and effective in proximity to a preselected injection site while simultaneously injecting by a needle or like instrument a liquid at the preselected injection site, and then continuing the vibration with more pressure applied to massage the injection site to dissipate the injected liquid and distribute it into the surrounding tissue. Preferably this is done while sounding bone underneath the tissue, as noted above.

The objects of the invention are accomplished by an instrument for minimizing pain during administration by injection of a liquid, such as, an anesthetic comprising a main body having a forward end, a light-transmitting rod or lightpipe mounted in said body freely for vibration and projecting out of said forward end, a tip composed of a tip sleeve removably mounted on the forward end of said main body and a pronged tip member having a forward bifurcation defining a preselected injection site on a human or animal removably mounted on the lightpipe, said tip sleeve and pronged tip member being covered and held together by an elastic overmold while allowing light from said light rod to illuminate the injection site, a vibration unit mounted in the main body and coupled to said light rod such that when initiated imparts vibrations via said light rod to said pronged tip member. The instrument can comprise means for controlling the vibration unit for an on-off duty cycle, the duty cycle can be about 1 second on and about ⅒ second off. The pronged tip member may include at least one surface to act as a retractor. The tip sleeve and main body can include mutually coating members to prevent reuse of said tip. A music player may be included in the main body for playing music through a speaker. The light rod is preferably composed of polycarbonate and the light rod is held by an O-ring at the forward end in order to be vibrated freely.

The objects of the invention are further accomplished by providing an instrument for minimizing pain during administration by injection of a liquid, such as, an anesthetic comprising a main body having a forward end, a light rod mounted in said body extending toward said forward end, a single use disposable tip composed of a tip sleeve removably mounted on the forward end of said main body and a pronged tip member having a forward bifurcation defining a space that brackets a preselected injection site on a human or animal removably mounted on the light rod, said tip sleeve and pronged tip member being covered and held together by an elastic overmold while allowing light from said light rod to illuminate the injection site, a vibration unit mounted in the main body and coupled to said light rod such that when initiated imparts vibrations to said pronged tip member via said light rod, said tip and main body having mutually coacting elements such that once the tip is placed on said main body, its removal automatically prevents reuse of said tip. The instrument can include means for controlling the vibration unit for an on-off duty cycle, which is preferably set for a duty cycle is about 1 second on and about ⅒ second off. The pronged tip member can include at least one surface to act as a retractor.

The objects of the invention with respect to a method may comprise the steps of vibrating tissue of a human or animal in proximity to, adjacent to and bracketing a preselected injection site while simultaneously illuminating an injection site and injecting by a needle or like instrument a liquid at the preselected injection site, wherein the vibration is pulsed. The pulsing is preferably about 1 second on and about ⅒ second off.

The objects of the invention with respect to an article comprise providing a single use disposable tip for use with an instrument that includes a vibration unit and a lightpipe (transparent or translucent rod that transmits light) that is vibrated by the vibration unit, the lightpipe projecting out of the forward end of the instrument, the tip comprising a tip sleeve for removably mounting on the forward end of instrument and a pronged tip member for removably mounting on the projecting lightpipe. The pronged tip member has a forward bifurcation defining a preselected injection site on a human or animal. The tip sleeve and pronged tip member are covered and held together by an elastic overmold that enables the pronged tip member to vibrate freely with respect to the tip sleeve and light from the lightpipe to illuminate the injection site. The single use disposable tip, i.e. the tip sleeve and the pronged tip member are spaced apart and an annular space between them is filled with overmold. The pronged tip member comprises a cup and an integrally formed pair of longitudinally extending prongs with the overmold of the prongs having a wider portion to provide at least one retraction surface. At least one longitudinal groove may be formed in the wider portion of the overmold. Also, the overmold at the ends of the prongs is preferably bulbous. The forward end of the tip sleeve preferably defines alternate grooves and ribs and the overmold fills the grooves and covers the ribs.

BRIEF DESCRIPTION OF THE DRAWINGS

The above-mentioned features and objects of the present invention will be discussed in terms of the attached figures wherein like reference numerals denote like elements and in which.

DETAILED DESCRIPTION OF PREFERRED
EMBODIMENTS OF THE INVENTION

Figure 1:
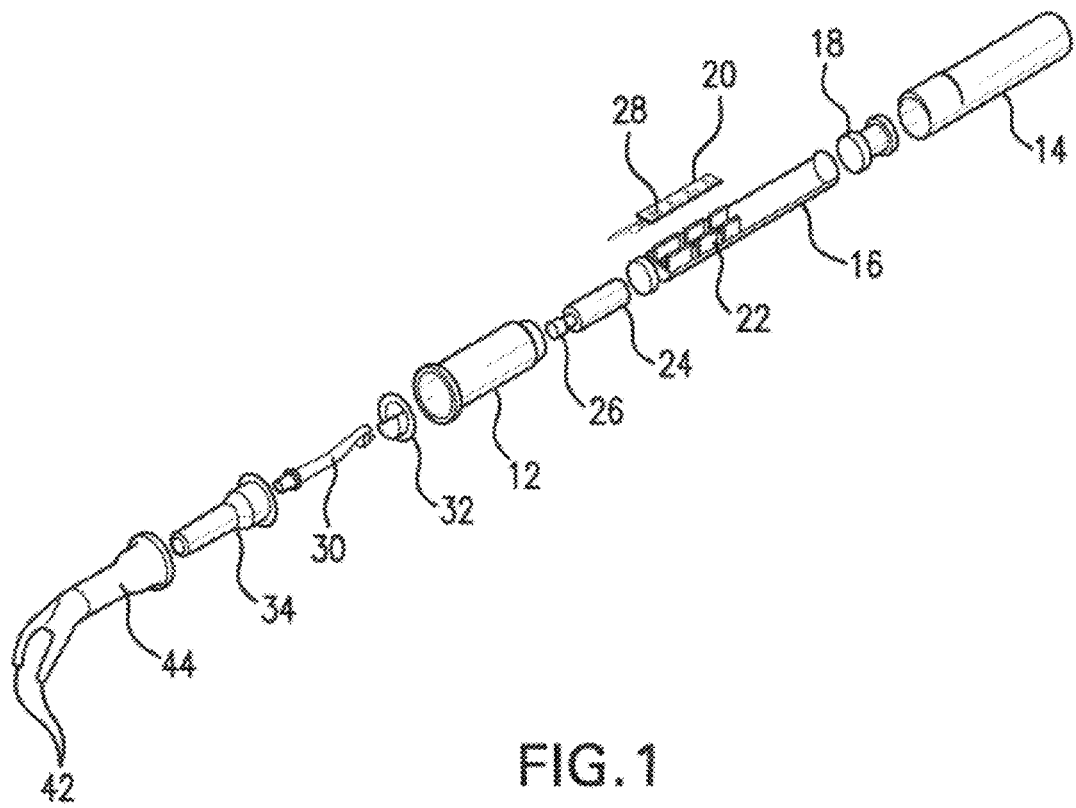
FIG. 1 is an exploded drawing showing an embodiment of the apparatus of the present invention.
Figure 23:
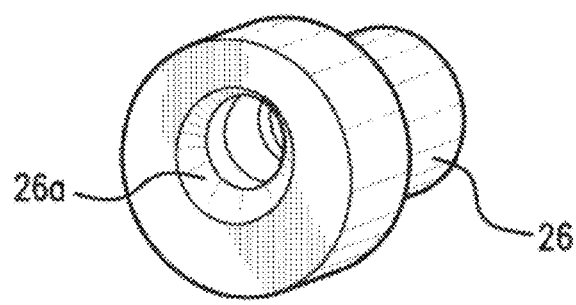
FIG. 23 is a perspective view of the cam attachment to the electric motor to induce vibrations.
Figure 12:
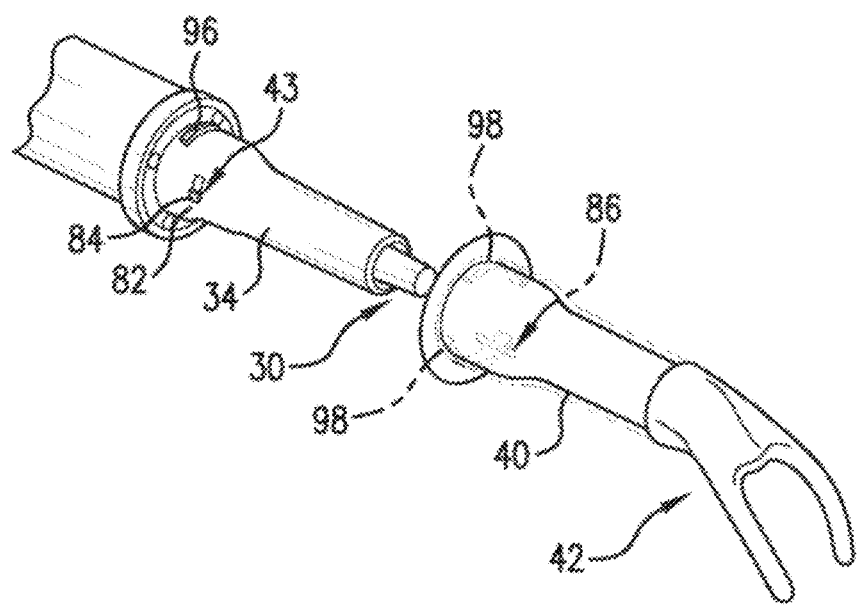
FIG. 12 shows in perspective a partially exploded view showing the tip removed from the nose of the instrument.

Referring to FIG. 1, an embodiment of the improved retractor vibrator is shown generally designated as 10 for performing the functions of the present invention, as will be explained hereinafter. In particular, retractor vibrator 10 is a handheld apparatus comprising a main body or handle 12 in the shape of a tube having a battery cover 14 as an end closure that is threaded to screw onto the open end of handle 12 in a complementary fit. Handle 12 is composed of hard plastic and partially receives a chassis 22, the uncovered portion being covered by the battery cover 14. Rechargeable batteries, not shown in FIG. 1, are located in battery compartment 16 of chassis 22. An induction coil 18 is mounted on the end of chassis 22 and positioned in the battery cover 14 to couple to a charge device in a conventional manner. A motor 24 driving a cam 26 is housed in the handle 12. Cam 26 includes a bore, see FIG. 23 (in the form of a ball socket 26a) whose axis is offset from the motor drive axis by from about 0.010 inches to about 0.025 inches, with an offset of about 0.020 inches being preferred. The vibration induced by the cam 26 and follower 100 is transmitted via a polycarbonate light rod 30 to polycarbonate tip frame 50 and will produce vibrations at the free ends of the two bifurcated legs 42 of tip frame 50 having amplitude of about 0.5 mm (0.020 inches). During vibration, the light rod 30 will be pivoting about a resilient mounting (rubber O-ring) at the end of the nose 34 holding the light rod 30 relative to nose 34 so that it can vibrate freely. A PCB board 20 containing electrical and electronic circuitry 28 is mounted on the chassis 22. The battery is connected via the circuitry 28 to control the motor 24 in the manner described in my copending application Ser. No. 11/575,564 filed Mar. 19, 2007, here incorporated by reference. When the motor 24 is driven, vibration produced by the cam 26 is coupled to polycarbonate light rod 30 via a coupling fitting and cam follower.

Figure 2:
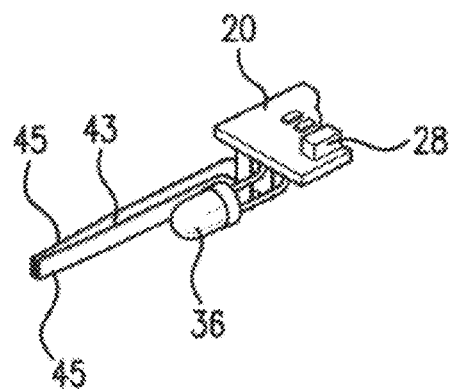
FIG. 2 shows in perspective details of the LED and electrical interlock switch.

The forward end of the handle 12 has an adapter 32 fixed to the chassis and the handle. A nose 34 is fixed to the adapter 32. The light rod 30 is received in the nose 34 and is resiliently coupled to it at its forward end. The nose 34 receives a disposable tip 40 comprised of three components, namely, a forward vibratable tip 50 detachably and rigidly mounted on the end of light rod 30 to transmit vibrations, with tip 50 having a bifurcation at its forward end, a tip sleeve 62 for detachably and rigidly mounted on nose 34 and an overmold 52 that holds tip 50 and sleeve 62 together and enables tip 50 to vibrate freely relative to sleeve 62. An LED 36 is mounted to the PCB 20 as shown in FIG. 2. Also projecting forwardly from the PCB 20 is electrical interlock 43 extending forwardly and consisting of two spring electrodes 45 normally biased apart to leave a small space between them. When the two electrodes 45 are brought together, they complete the electrical circuit that drives the motor 24. There is also a master switch 46 in the electrical circuit that controls overall power for the unit and is incorporated with button 48 (see FIG. 9) resiliently mounted in the handle 12.

Figure 3:
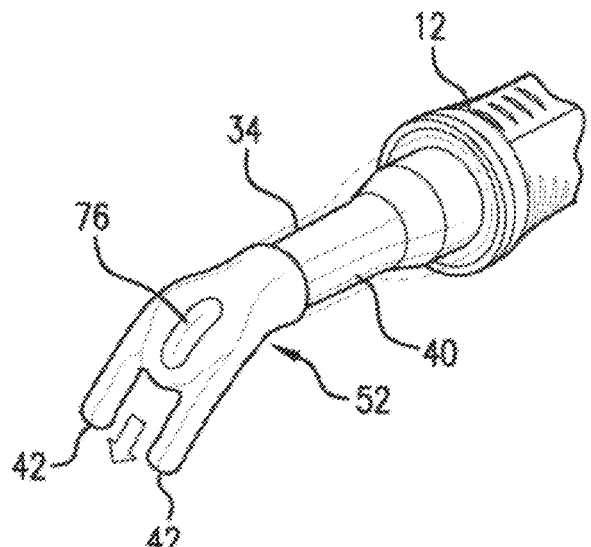
FIG. 3 shows in perspective the removable or disposable tip on the end of the instrument.
Figure 4:
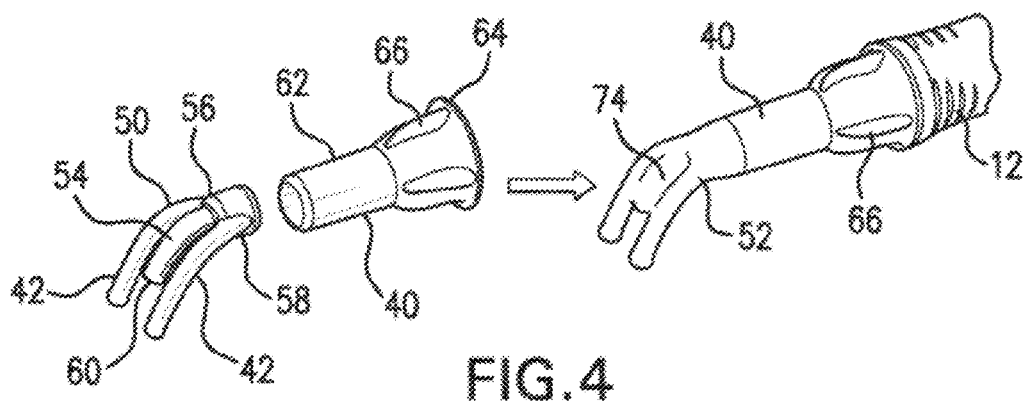
FIG. 4 shows in perspective the removable tip and the end of the instrument.
Figure 5:
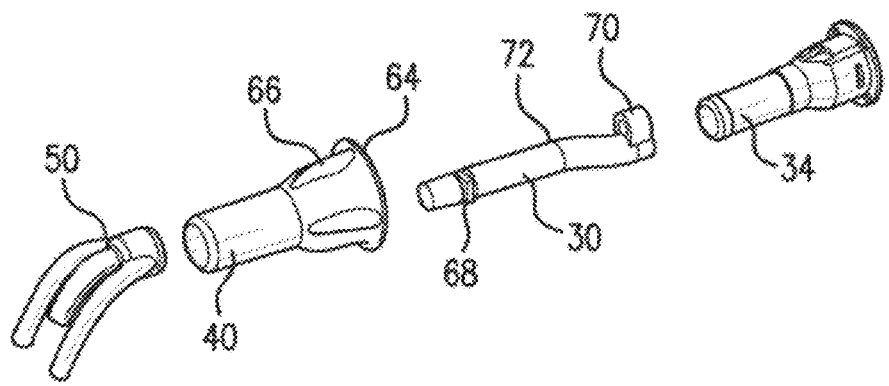
FIG. 5 shows in perspective the light-transmitting rod in relation to the removable tip on the end of the instrument.

FIGS. 3, 4 and 5 show various details of the disposable tip 40 mounted on the nose 34. As shown the forward end of the disposable tip 40 is a frame 50 overmolded with plastic 52, preferably resilient or with a soft finish as it will lie adjacent the tissue surrounding the injection site. It may be simply molded completely of plastic. Between the two legs 42 of the bifurcation there is a cantilevered tube 54 emanating from a hole 56 at the junction with the base 58 of the bifurcation of the frame and terminating in a lens 60. This tube can be eliminated as shown in FIGS. 24 to 28. The overmold 52 holds the tip frame 50 to the remainder of the tip 40 consisting of annular body 62 (tip sleeve) that terminates on its rear end with a flange 64 reinforced with ribs 66. The overmold enables the frame 50 to vibrate freely relative to sleeve 62. The forward end of the light rod 30 fits in nose 34 with the O-ring held by wedges 35 received in groove 68 to center the light rod 30 in nose 34 and light rod 30 projects from the forward end thereof and is received in the rear end of the overmolded bifurcation (tip frame 50) in tight engagement to impart vibrations from the light rod 30 to the tip frame 50. Light rod 30 is in alignment with hole 56 to transmit light through hole 56 and, optionally, tube 54 through lens 60 onto the injection site. In FIG. 5 the light tube 30 is shown with a circumferential groove 68 adjacent its forward end (to receive a resilient gasket, O-ring) and a coupling fitting member 70 at is other end. Light tube 30 has a bend 72 toward its rear that offsets the axis laterally so that it will align with the LED 36. As shown in FIG. 4 the overmold 52 of the bifurcation has horizontal grooves 74 to collect saliva if used in the mouth. Likewise in FIG. 3, the bifurcation can have a downward extending groove or reveal 76 for the same purpose. Removal of the saliva is difficult and this helps to prevent reuse of the tip.

Figure 6:
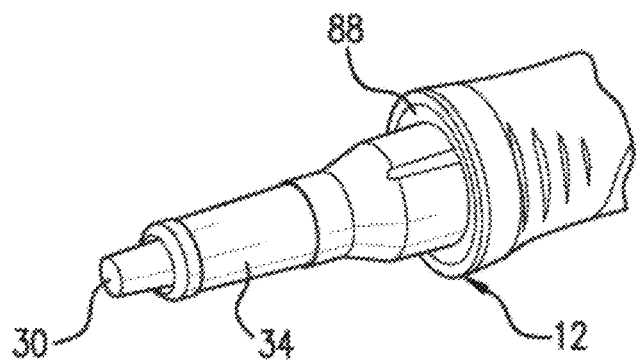
FIG. 6 shows in perspective the end of the instrument.
Figure 7:
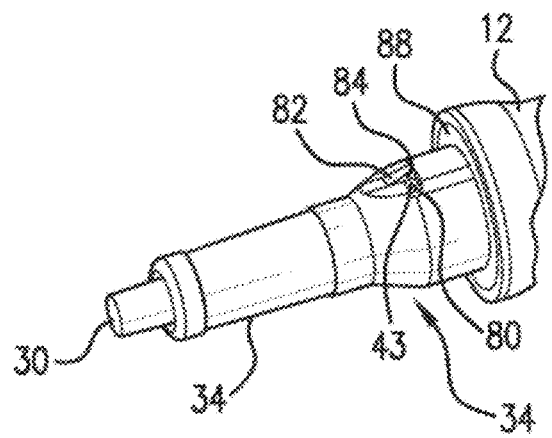
FIG. 7 shows in perspective a rotated view of the end of the instrument.
Figure 8:
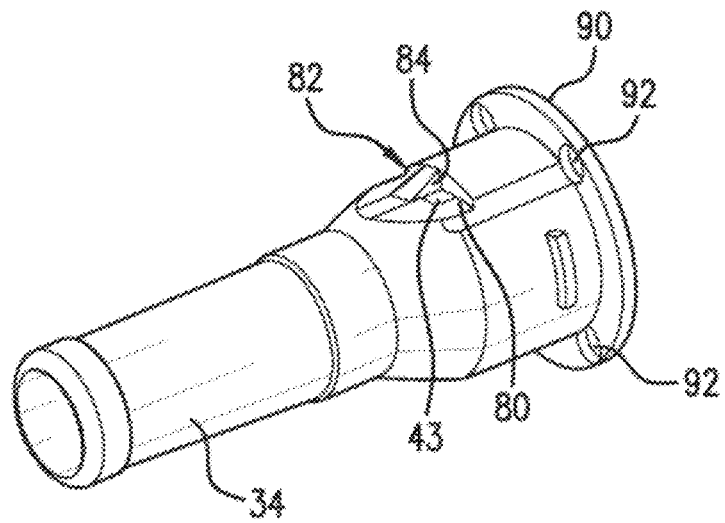
FIG. 8 shows in perspective the nose of the instrument.
Figure 16:
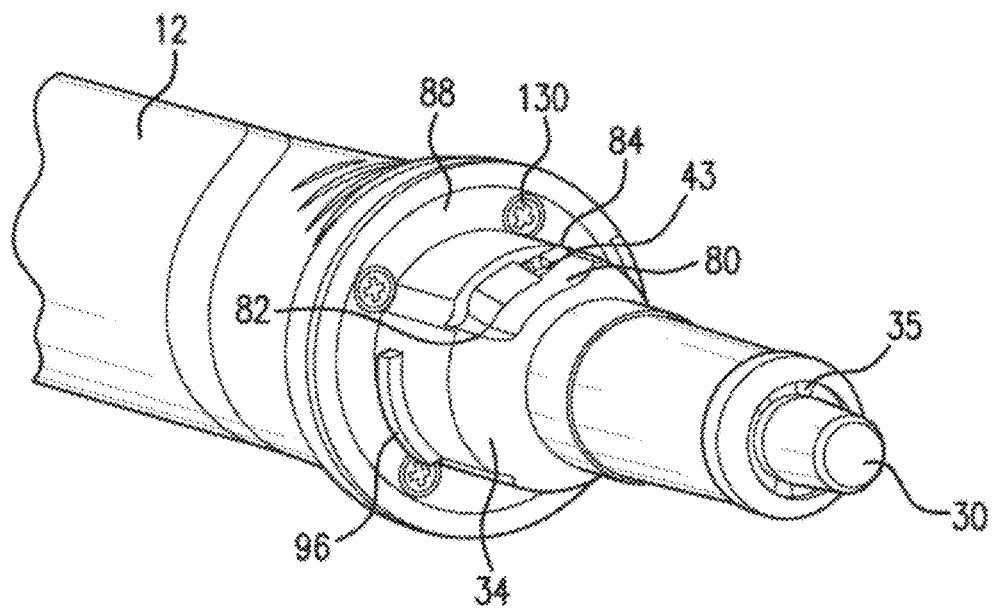
FIG. 16 shows in perspective the handle and nose of the instrument.
Figure 17:
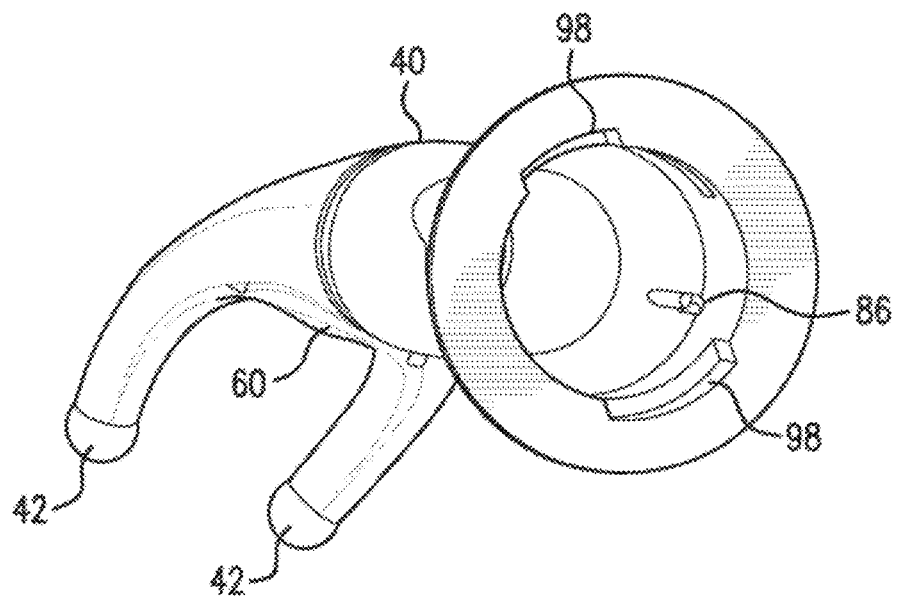
FIG. 17 shows in perspective the disposable tip seen from the rear.

FIGS. 6, 7, 8 and 12 show one way for positively preventing the disposable tip 40 from a second use. See also FIGS. 16 and 17 in this regard. The electrical interlock 43 is brought out onto the surface of the nose 34 at a cutout 80 with the two electrodes 45 lying one above the other with a small space between. A ramp 82 is formed adjacent the cutout area 80 and the transition between the ramp 82 and the cutout 80 is a vertical (90 degree) flat surface 84. The sleeve 62 of disposable tip 40 is provided on its inner surface with a frangible rib 86 that coacts with ramp 82, interlock 43 and flat surface 84 as follows. The disposable tip 40 is mounted to the nose by placing over, seating and giving a ¼ turn. The orientation and alignment of these two parts is such that the rib rides over the ramp 82, drops down over the flat surface 84 onto the electrical interlock 43, forcing the two electrodes 45 together to actuate vibration of the instrument. When the tip 40 is to be removed, the tip is given a reverse ¼ turn, during which the frangible rib 86 will strike the vertical surface 84 and be broken off as the tip continues completing the ¼ turn necessary to disengage from the nose 34. Thus, after the tip 40 has been removed, it will no longer be able to be replaced on the nose 34 to force the electrical interlock to function. FIG. 8 also shows that the rear end of the nose 34 has a flange 90 with openings 92 to enable attachment to the chassis 22 and handle 12. As shown in FIG. 6, a cover ring 88 covers the flange of the nose 34.

Figure 9:
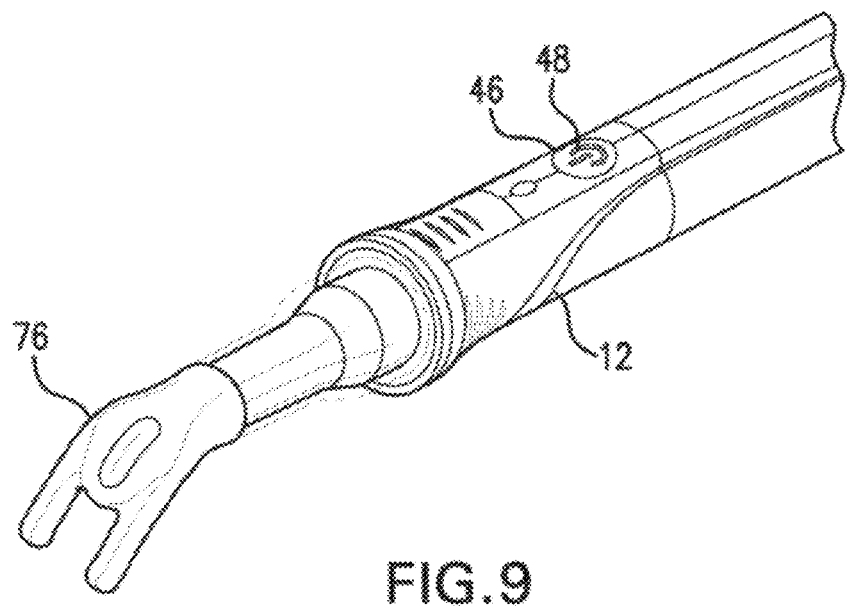
FIG. 9 shows in perspective a top view of the instrument.
Figure 10:
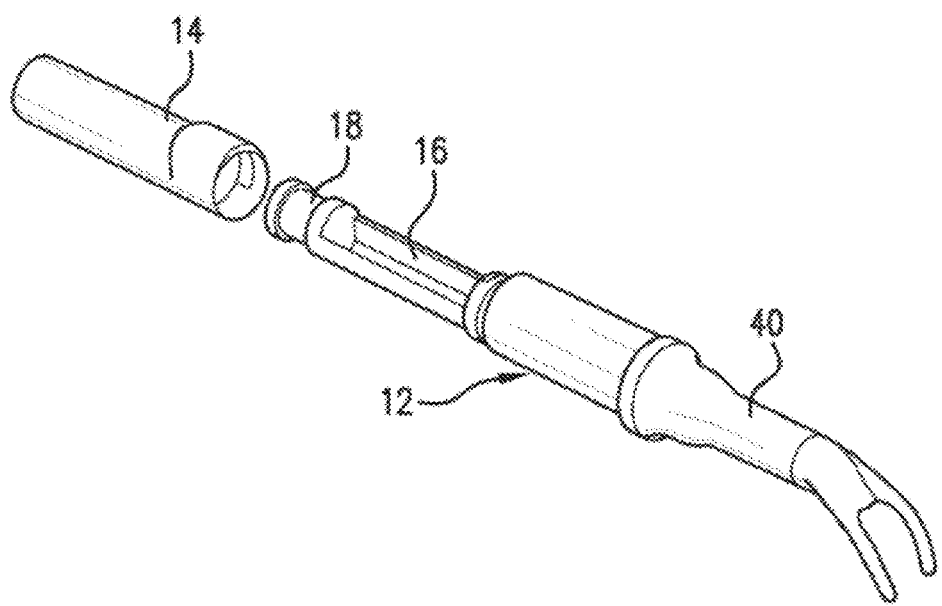
FIG. 10 shows in perspective a partially exploded view showing the instrument with the battery cover removed.
Figure 11:
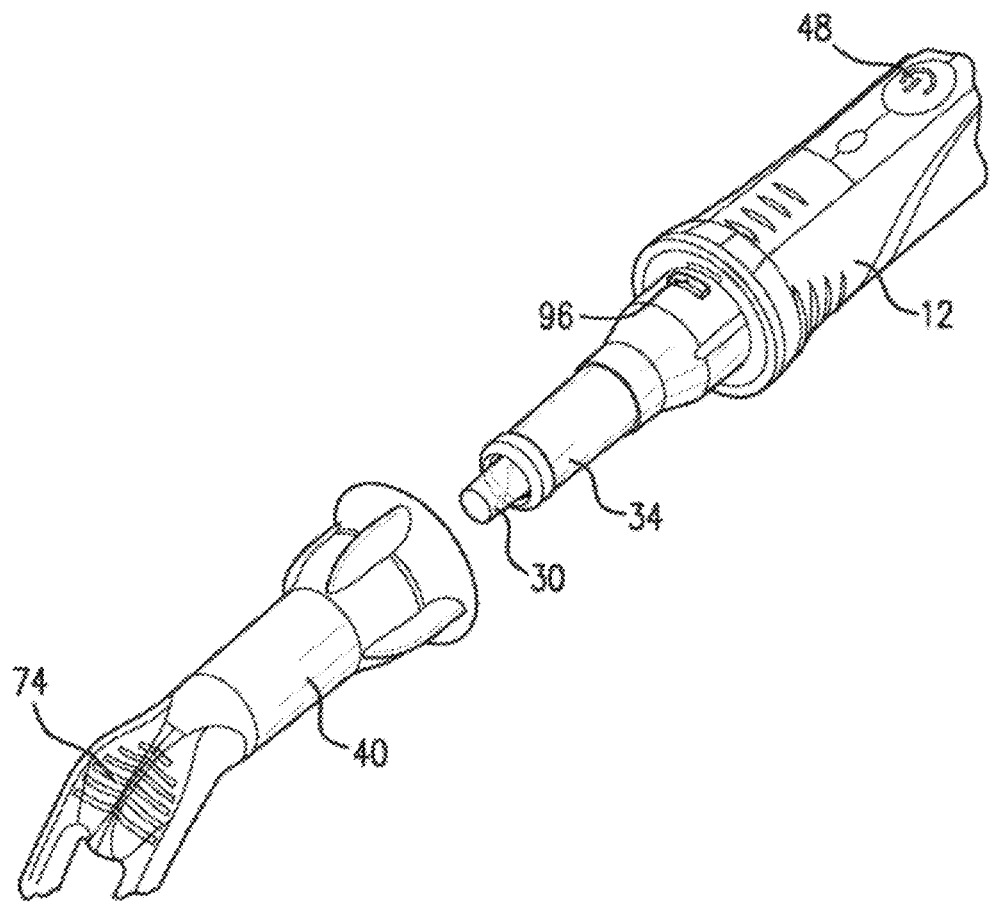
FIG. 11 shows in perspective grooving on the disposable or removable tip.

FIG. 9 shows the device or instrument assembled with a master switch 46 mounted on the handle 12 beneath a resiliently mounted button 48. FIG. 10 shows the battery cover 14 removed and the battery compartment 16 exposed. The battery compartment is part of the chassis 22. FIG. 11 is a view similar to FIG. 10 but showing the front end of the device or instrument and illustrating the relationship of the disposable tip 40 to the light rod 30 and nose 34. A circumferential rib 96 and groove 98 are formed diametrically opposite on the nose 34 and coact with a complementary circumferential groove 98 and rib 96 (see FIG. 12) in the inner surface of the tip 40 to lock the tip on the nose in a bayonet fitting.

Figure 13:
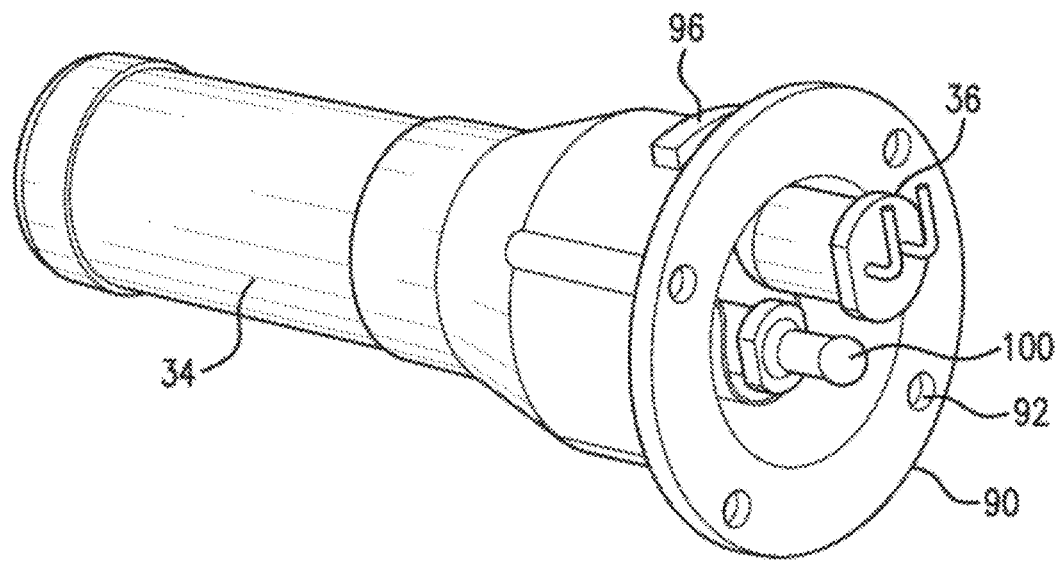
FIG. 13 shows in perspective the rear end of the nose.

FIG. 13 shows the rear end of the nose 34 from which the fitting member 70 attached to the end of the light rod 30 and holding a projecting stub with ball end 100 as a cam follower for contacting and following the cam 26 (see FIG. 23 for detail) to impart the vibratory motion of the cam 26 to the light rod 30. The bottom of the light rod 30 is in alignment with the LED 36 as previously described. Although continuous pulsing can be used, it has been discovered that a pulsed vibration sequence is more effective. A pulsed sequence of about one second on and then about a tenth of a second off, is sufficient to pulse the vibration without allowing the vibration of the tip to ever drop down to zero. In this manner, the device or instrument pulses about every second, re-stimulating the nerves in the area, and apparently the brain never gets used to it, so the vibrations remain effective. To this end the electronics controlling the pulsing is modified to include the necessary means for pulsing and obtaining the desired on/off duty cycle as noted. The motor is energized using 110 volt AC (110 Hz frequency). The frequency can vary from about 100 Hz to about 300 Hz. The vibration at the free ends of the prongs or forks 42 can vary from about 0.1 mm to about 0.75 mm. The duty cycle on pulsing is about 0.908 Hz (cycle time=about 1.1 sec. with a pulse off of about 0.1 sec. The off portion of the cycle should not be greater than about 0.5 sec.

Figure 14:
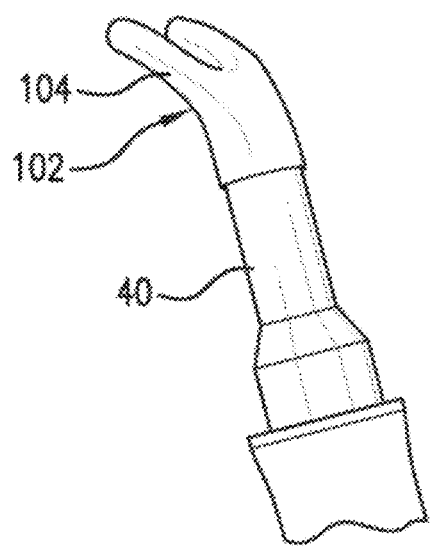
FIG. 14 shows in perspective the removable tip.
Figure 29A:
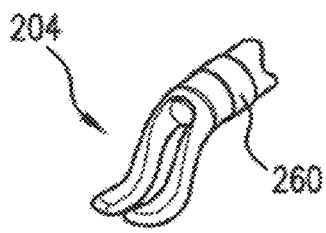
FIGS. 29a-m show in perspective views different tip shapes for the tip member shown in FIGS. 24-26.
Figure 29B:
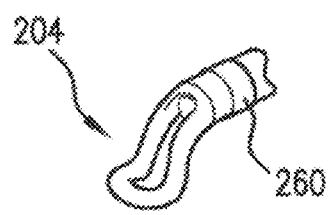
Figure 29C:
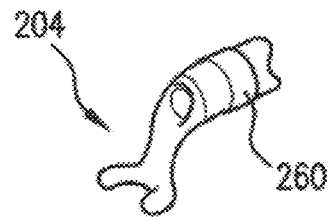
Figure 29D:
Figure 29E:
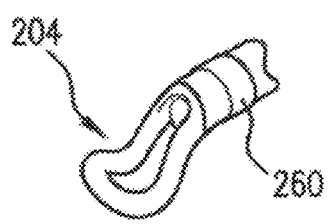
Figure 29F:
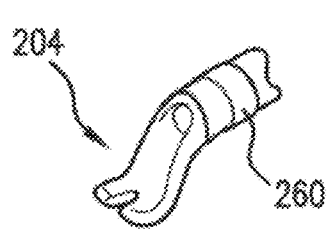
Figure 29G:
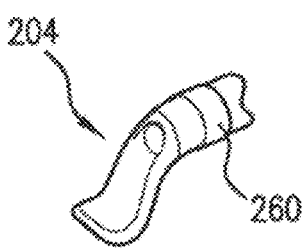
Figure 29H:
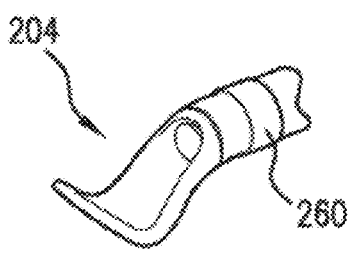
Figure 29I:
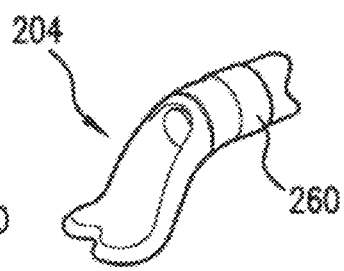
Figure 29J:
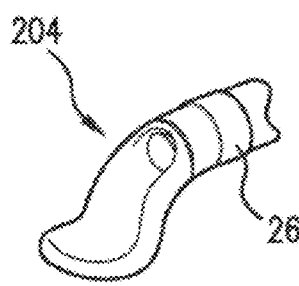
Figure 29K:
Figure 29L:
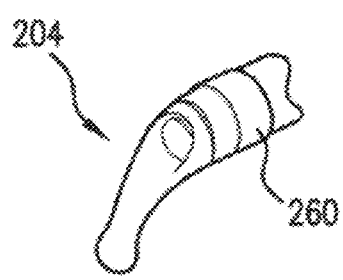
Figure 29M:
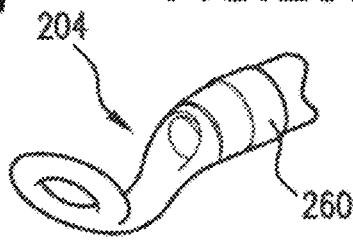

FIG. 14 shows in perspective the bifurcated end of the device and illustrates the profile. Essentially the overmolded tip runs straight 102 before it curves downwardly 104 at the bifurcated prongs 42, in order to obtain greater light being shined on the injection area of the tissue. The fact that this device exhibits enhanced amplitude and percusses the tissue contacted, causes a deeper penetration of the vibratory stimulus into the oral mucosa of a dental patient, thereby stimulating the nerve receptors, A-beta nerve receptors, which are located deep within the tissue. Also, vibration is sent out in a full 360 degrees around the tip 40, mainly, from three places off of the tip, namely, from each free end of the fork 42, as well as, from the paddle or retractor portion (area between tips of forks or prongs and joint with tip sleeve 62 which at times will stimulate the lip or cheek or bone when resting against it. The enhanced vibration is not limited to just in between the two forked prongs 42. Alternative tip free end shapes are shown in FIGS. 29*a*-*m*. FIG. 29*a* shows a bent fork, FIG. 29*b* shows a bent loop, FIG. 29*c* shows a bent flat U-shape, FIG. 29*d* shows a bent flat circular shape, FIG. 29*e* shows a bent loop, FIG. 29*f* shows a bent flat with a V-groove, FIG. 29*g* shows a bent flat plate, FIG. 29*h* shows a bent up plate, FIG. 29*i* shows a bent flat heart shape, FIG. 29*j* shows a bent flat rounded plate, FIG. 29*k* shows a downward member with a top groove, FIG. 29*l* shows a downward rod with a terminal bulb and FIG. 29*m* shows a bent up circular loop.

Figure 15:
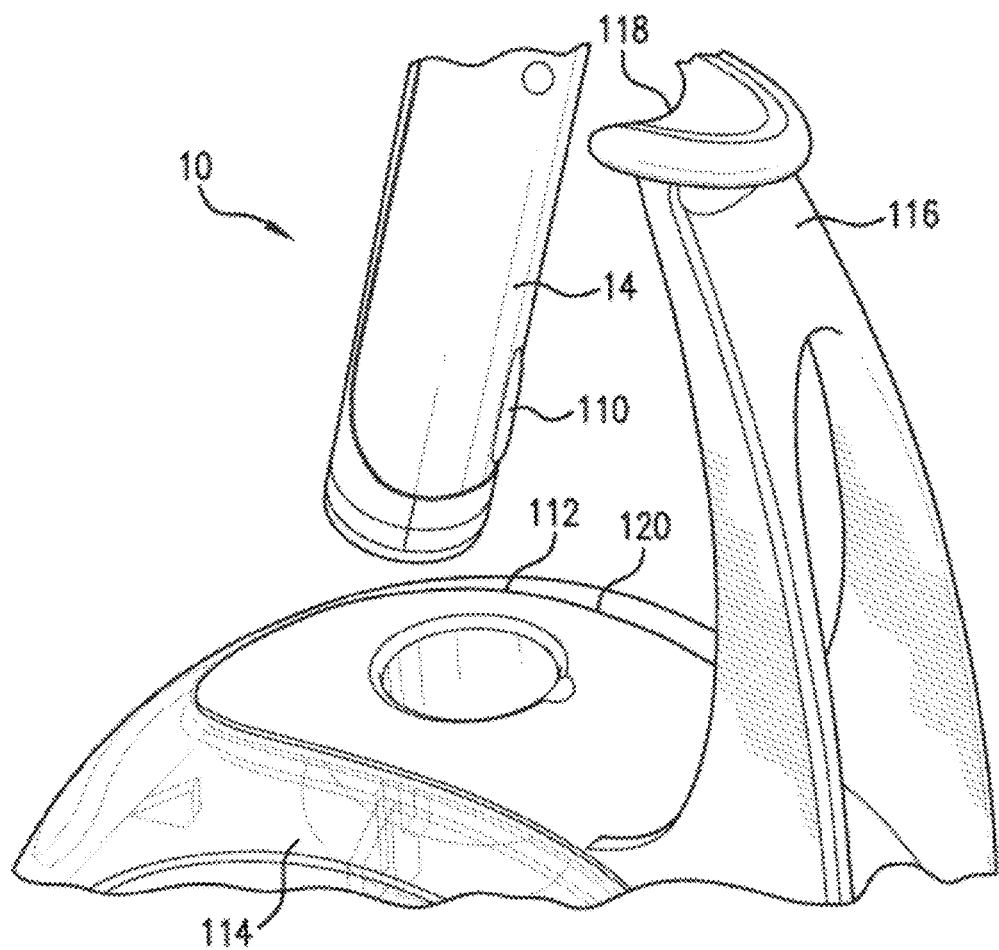
FIG. 15 shows in perspective in partially exploded view the mounting of the instrument during non-use and recharging.

FIG. 15 shows a simple mount for storing the device or instrument between uses. The rear end of the battery cover 14 is provided with a rib 110. The rear end of the device is inserted in a well 112 in a stand 114 that has a recess 120 extending downwardly to mate with the rib 110 for orientation purposes. The stand 114 has a vertical support 116 that terminates in a curved cradle 118 to receive and hold the forward part of the device or instrument 10. The stand is provided with means to connect to a power source to charge the batteries in the device 10 via induction in a manner well known in the art.

Figure 18:
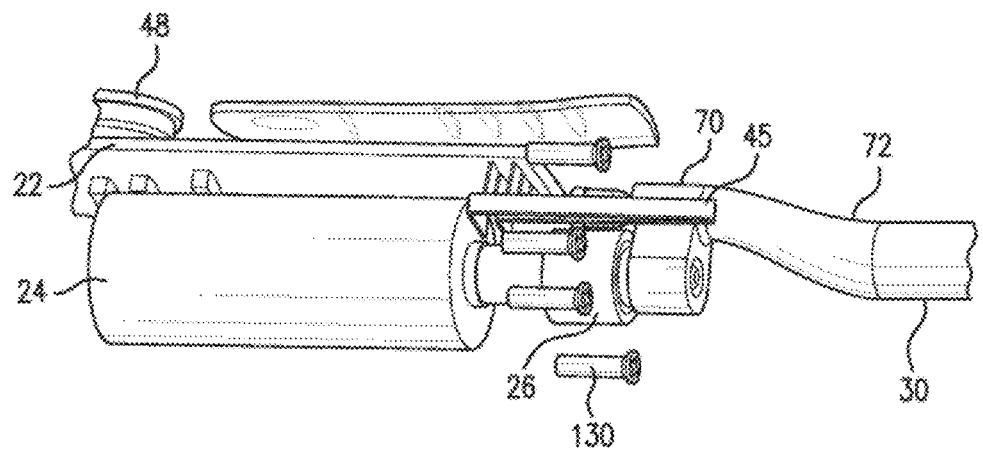
FIG. 18 is a partial view in perspective showing the motor mount and coupling with the light rod.
Figure 19:
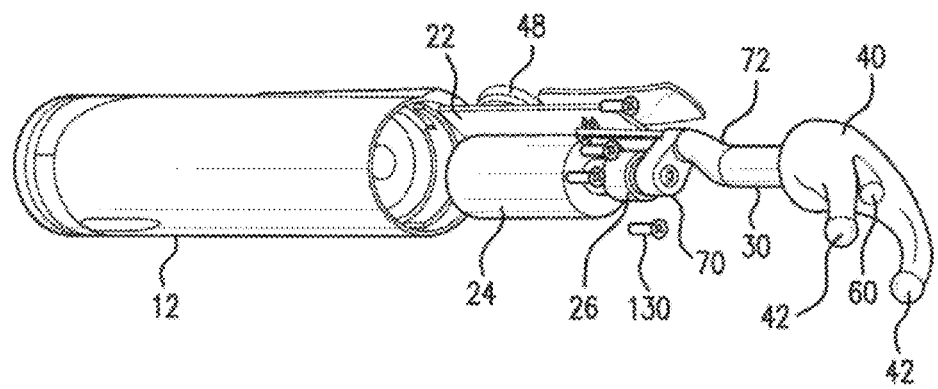
FIG. 19 shows in perspective in partially exploded view the handle, motor and coupling to the light rod and tip illustrating the light port.
Figure 20:
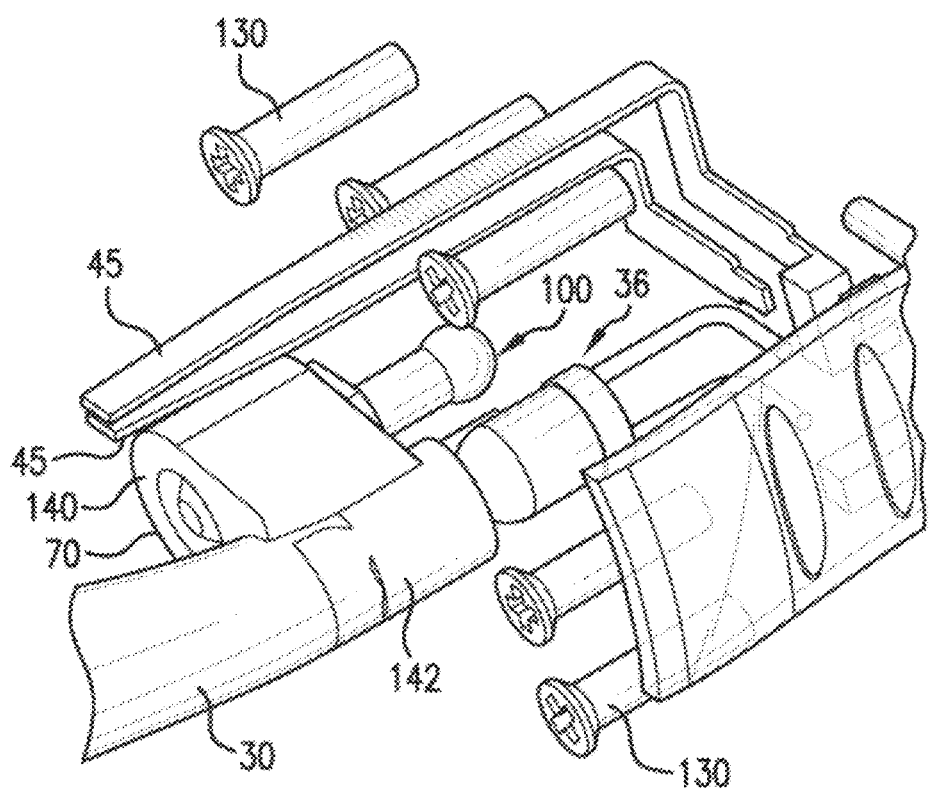
FIG. 20 is a view in perspective showing in an exploded view details of the coupling member on the inner end of the light rod.

FIGS. 18, 19 and 20 show details of the structure and the function of the device or instrument 10. Shown in FIG. 18 is the motor 24 mounted to the chassis 22 with the motor shaft connected to and driving the cam 26, The attachment fitting member 70 fixed to the light rod 30 is shown with the projecting stub with ball end 100 received in the cam 26. Light rod 30 is shown with bend 72 to displace its axis laterally so that the end of the light rod is aligned with LED 36. Also the electrical interlock is shown extending forwardly. The button 48 with switch 46 is shown in juxtaposition to the chassis 22 and the PCB positioned on to of the chassis. Screws or bolts 130 are shown and connect the nose 34 to the chassis 22. FIG. 19 adds the detail of the assembly shown in FIG. 18 being inserted into the handle 12 and the bifurcation member 42 in juxtaposed relation to the end of the light rod 30. FIG. 20 is an exploded view showing the above described relationships in even more detail. The attachment fitting 70 consists of an annular member 140 that captures and holds, preferably rotatably, the projecting stub with ball end 100. The member 140 is held on the end of the light rod 30 by a band 142 that clamps it to the rod 30.

There may also be contained within the handle 12 a music recorder/player that is loaded with a recording that plays through a speaker situated in the handle behind perforations. A switch can be provided suitably connected to turn the recorder/player on/off.

As shown in the parent application, the device or instrument 10 can be combined with a toy 160 in a manner useful for taking care of children for the purpose of distracting them while performing an injection. For children the disposable tips are sized appropriately and the vibration is reduced appropriately. The toy 160, for example, is a finger puppet, such as a thumb animal hollow inside and open at the rear. The toy is mounted on the rear end of the device or instrument 10. When the procedure is finished, the toy 160 can be removed and the toy given to the child. Any suitable toy can be used for this purpose, such as a doll, a fire truck and the like, as long as, it can or is modified to receive the retractor vibrator in a detachable manner.

The preferred embodiment of the single use or disposable tip (novel article) is shown in FIGS. 21-22 and FIGS. 24-28. As shown, the article (single use tip), generally designated 200 consists of an elongated tip sleeve 202 composed of polycarbonate an elongated forked tip member 204 composed of clear polycarbonate and an overmold 206 composed of rubber or a thermoplastic elastomer. The single use tip 200 is mounted on the nose 34 of the instrument, from which extends lightpipe 30 by the tip sleeve 202 being received onto the nose 34 and the rear end 210 of the tip sleeve 202 being detachably attached to the nose 34 by means of a bayonet joint consisting of peripherally extending arcuate ribs 96 coacting with slots 98, see FIG. 12 and relevant description supra. The tip sleeve is mounted to nose 34 to leave a small gap 201 between the end of the tip sleeve and the face of the instrument, see FIG. 21. The tip sleeve 202 has a flange 205 at its rear end and is reinforced by ribs 203. Tip sleeve 202 is provided on its interior surface with a longitudinally extending frangible rib 86 that coacts with ramp 82 on nose 34 to close interlock 43, see FIGS. 12, 16 and 17 and relevant description supra. The forked tip member 204 consists of a transparent cup 212 having a sidewall 222 and bottom wall 224 that is rounded exteriorly to form of a lens 214. A pair of prongs 216 is integrally formed with the sidewall of cup 212. The prongs 216 extend spaced apart forwardly and downwardly terminating in free ends 218. The angle of the longitudinal axis of the prongs relative to the longitudinal axis of the tip sleeve 202 is about 55 degrees. The space 220 between the two prongs 216 adjacent their free ends 218 defines the preselected injection site. Light emanating from the end of lightpipe 30 is directed by lens 214 generally toward the injection site. The inside of side wall 222 of cup 212 is tapered to engage the end of the lightpipe 30 in a tight manner. The lightpipe 30, driven by a motor mounted in the instrument via an eccentric cam 26 of the instrument, see FIGS. 18-20 and relevant description supra, is held in nose 34 adjacent the forward end by an O-ring 230 constrained by a rib 232 and the forward end of the nose 34 that allows lightpipe 30 to vibrate freely. The O-ring 220 can be stuffed into a D-shaped groove formed in the interior surface at the end of the nose 34. The overmold 206 is rubber or a thermoplastic elastomer having a durometer of preferably about 40 A but may vary from about 30 A to about 50 A. The overmold 206 extends from the free ends 218 of the prongs 216 to and over the forward end 240 of the tip sleeve 202, portion 206a of the overmold covers the end of the tip sleeve 202. The forward end 240 of the tip sleeve 202 is grooved on its exterior surface to provide alternate peripheral grooves 242 and ribs 244 that serve as a strong gripping surface. Overmold portion 206a covers and fills the grooves and the ribs. Tip sleeve 202 is slightly spaced from the forked tip member 204 and the annular space between them is filled with overmold portion 206b. The spacing isolates the member 204 from the sleeve 202 and enables the forked tip member 204 to vibrate freely relative to the sleeve 202. Overmold 206 covers the exterior surface of the forked or pronged tip member 204, except for lens 214 of the cup 212. The entire surfaces of the prongs 216 are covered by overmold 206. The overmold 206 at the free ends 218 of prongs 216 is thicker and formed with a bulb shape 252. The overmold 206 at approximately halfway up the prongs 216 starting at point 254 up to the cup 212 is made wider on the inside of the prongs 216, as indicated by reference numeral 266, to provide surfaces 256 that can assist in retraction of skin or tissue. Each of these surfaces 256 is provided with a longitudinally extending groove 258 to assist in the removal of saliva or other liquids that may be present. In addition, the tip member is provided with one or more holes 270, preferably not through holes, that have a bore of capillary size, so that saliva or other body liquids will become absorbed into and trapped therein during use. This will prevent anyone from trying to re-sterilize a used tip.

Figure 21:
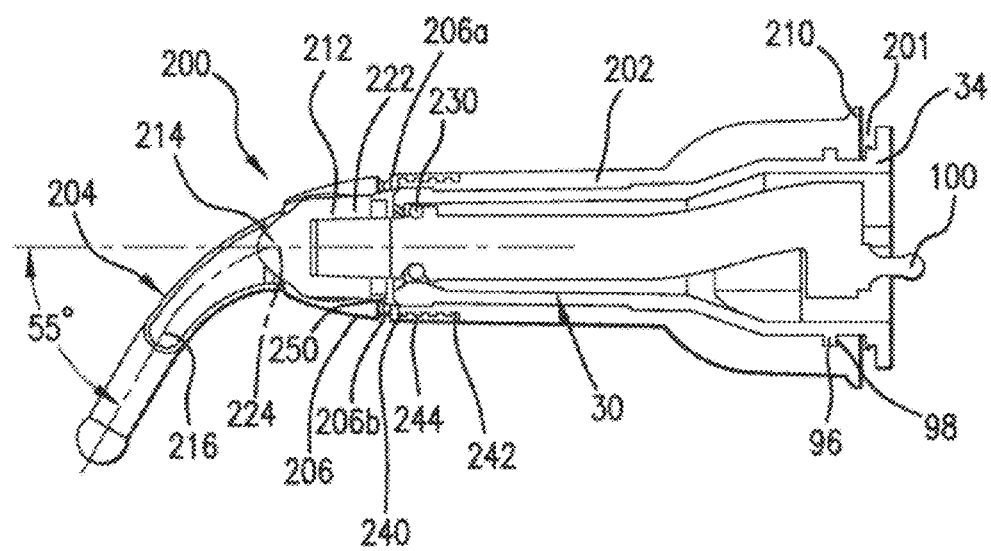
FIGS. 21 and 22 show in cross section and perspective, respectively, details of the preferred embodiment of the present invention showing improvements to an instrument in the form of a retractor vibrator and improvements to an article in the form of a single use or disposable tip for use in a method for medical and dental procedures, said improvements contributing for reducing or minimizing pain during tissue or skin puncturing procedures, such as, administration by injection, into the gums, skin or other tissue of a patient, of a liquid, such as, and in particular, an anesthetic.
Figure 22:
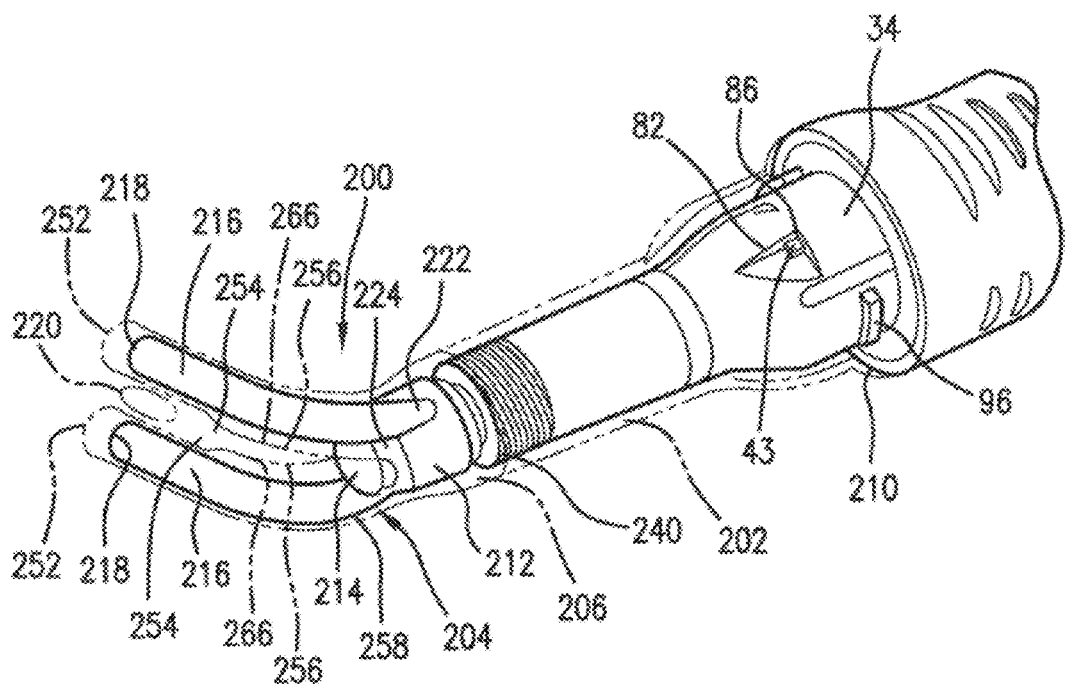
Figure 24:
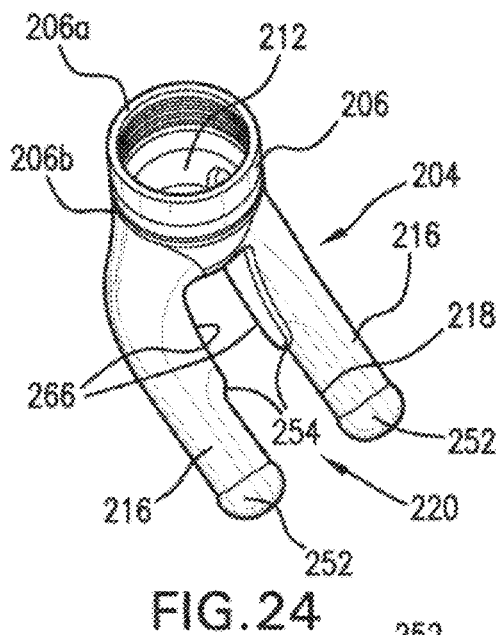
FIGS. 24-26 show in perspective and side views the vibrated tip member.
Figure 25:
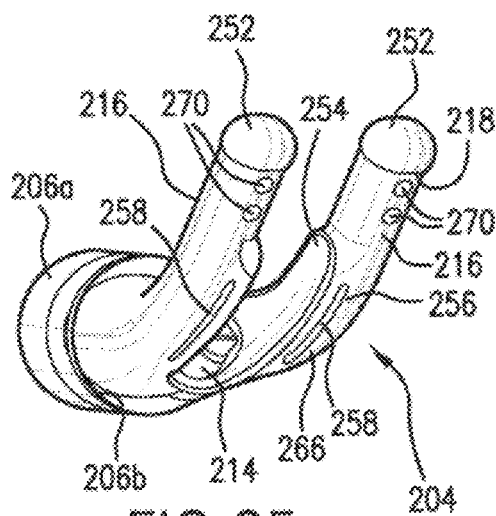
Figure 26:
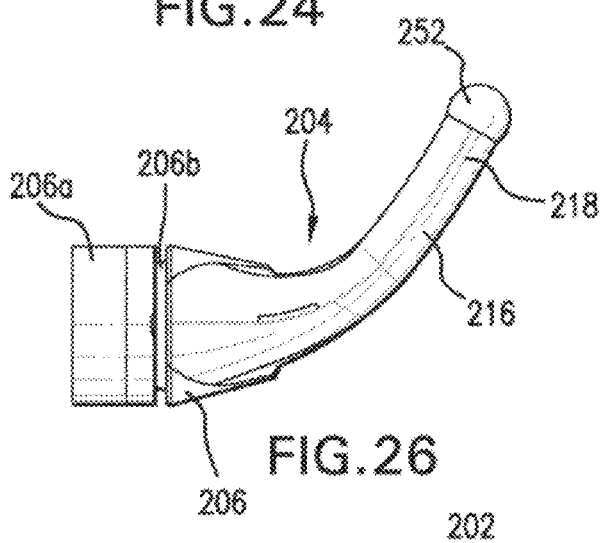
Figure 27:
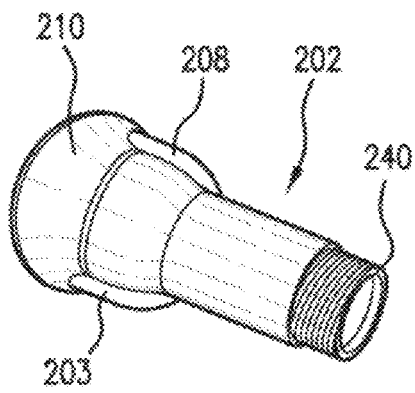
FIGS. 27 and 28 show in side views the tip sleeve.
Figure 28:
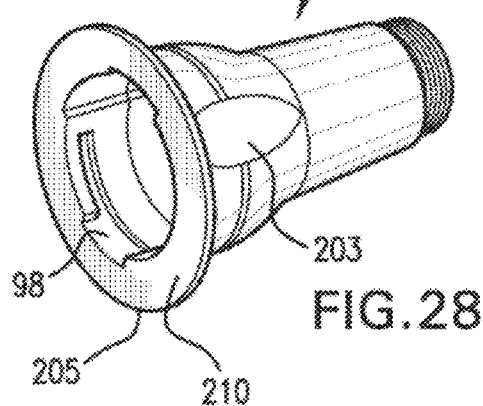
Figure 30:
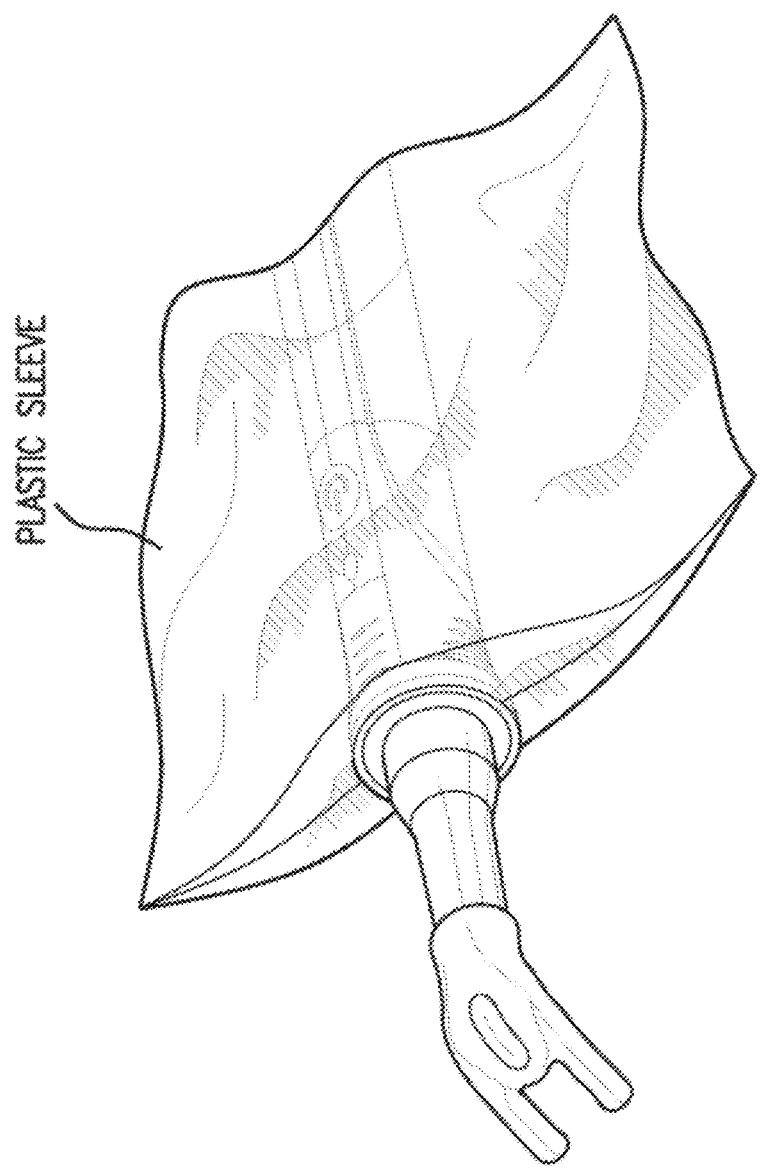
FIG. 30 shows a plastic wrapper mounted on an instrument to enable the dentist or doctor to use the instrument without affecting its sterility.

FIG. 30 shows how a plastic sleeve or wrapper can be placed around the instrument to protect its sterility and avoid contamination during use. The plastic sleeve or wrapper has a hole punched in it so it can fit over nose 34, and the disposable tip can be mounted over the nose 34 as described. To this end, the flange at the rear of the disposable tip is spaced slightly from the face of the instrument to provide a slot 201 to accommodate the plastic sleeve or wrapper in between the instrument and the tip, as illustrated in FIG. 21.

If the device or instrument is to be used for a medical application, that is, to some part of the body other than the mouth, the disposable tip will curve upwardly, 180 degrees opposite from the dental application described above, and the legs 216 of the tip member 204, or other tip member shape, will be uncoated by the overmold with the overmold 260 bridging and holding together the cup of the tip member and the ribbed end of the tip sleeve, as shown in each of the drawings of FIG. 29. It should be apparent to one skilled in the art, from the above description that the present invention can be utilized in a variety of procedures requiring a skin or flesh puncture. Such other procedures include such things as inoculations, shots to give patients medication, etc. Such skin punctures procedures can be performed on any portion of the body such as the arm, legs, buttocks, torso, etc.

The method of the invention consists in vibrating tissue of a human or animal in proximity to a preselected injection site on the human or animal body while simultaneously injecting by a needle or like instrument a liquid at the preselected injection site. The vibration is most effective if transmitted to a circular volume of tissue and underlying bone at the injection site, and particularly on opposite sides of injection site. Also, it is preferred that a noise generator be mounted in the main body of the instrument so that the vibration is accompanied by noise that will provide a distraction. In the most preferred embodiment of the method, a pulsed vibration sequence is used. A pulsed sequence of one second on and then a tenth of a second off, was sufficient to pulse the vibration without allowing the vibration of the tip to ever drop down to zero. In this manner, the device or instrument pulses every second, re-stimulating the nerves in the area, and apparently the brain never gets used to it, so the vibrations remain effective. The tip is vibrated and has a free end characterized by a shape to induce vibrations in the tissue and underlying bone, whereby the free end can be placed in proximity to a preselected injection site on a human or animal and the tissue and underlying bone at said preselected injection site is vibrated while an injection is given. The vibrations are continued even after the injection has been completed to massage the tissue to dissipate the injected liquid into the tissue and prevent tissue distension and swelling of the tissue, which is a source of pain. Preferably, the subsequent vibration is effected with more pressure on the tissue by the person injecting to effect better massaging. The subsequent vibration is most effective if the pressure applied is sufficient to sound bone beneath the tissue. An ordinarily skilled-in-the-art dentist can sense when he is applying pressure to tissue, such as the gums, and his instrument is effectively touching and in good contact or hitting on underlying bone. When such bone contact is sensed, the pressure is maintained for at least 1 up to about 30 seconds or until any tissue distension is no longer observed.

While the present invention has been shown and described herein in what are conceived to be the most practical and preferred embodiments, it is recognized that departures, modifications, adaptations and variations may be made therefrom without departing from the intended scope of the invention as set forth in the appended claims.

What is claimed is:

1. An instrument for minimizing pain associated with a skin-puncturing procedure, the instrument comprising:
   an elongated, main body having a forward end; a lightpipe for illumination and vibration, the lightpipe mounted within an interior of the elongated, main body and having a projected end, the projected end projecting out of an interior of the forward end of the elongated, main body and projecting light therefrom;
   a tip having:
   a) a tip sleeve removably mounted on the forward end of the elongated, main body;
   b) a tip member rigidly and removably mounted on the projected end of the lightpipe, the tip member having a shape to vibrate a defined, pre-selected skin-puncturing site on a human or animal; and
   (c) an annular space between the tip sleeve and the tip member;
   an elastic overmold molded to a shape of the tip and connecting the tip sleeve and the tip member, the elastic overmold extending from a free end of the tip member to a forward end of the tip sleeve and filling the annular space between the tip sleeve and the tip member, whereby the annular space isolates the tip member from the tip sleeve enabling the tip member to vibrate relative to the tip sleeve and allowing light from the lightpipe to illuminate the defined, pre-selected skin-puncturing site; and
   a vibration unit mounted within the interior of the elongated, main body and coupled with the lightpipe to impart vibrations via the lightpipe to the tip member.

2. The instrument according to claim 1, further comprising a controller for controlling the vibration unit for an on-off duty cycle.

3. The instrument according to claim 2, wherein the on-off duty cycle is about 1 second on and about ⅒ second off.

4. The instrument according to claim 1, wherein the tip member includes at least one surface to act as a retractor.

5. The instrument according to claim 1, wherein the tip member includes at least one hole not completely there through.

6. The instrument according to claim 1, wherein the lightpipe is composed of polycarbonate.

7. The instrument according to claim 1, wherein the lightpipe is held by an O-ring at the forward end of the elongated, main body.

8. The instrument according to claim 1, wherein the elongated main body has a central axis and the lightpipe is positioned along the central axis of the elongated main body.

9. The instrument according to claim 1, wherein the elastic overmold is composed of rubber or a thermoplastic elastomer.

10. A method for minimizing pain associated with a skin-puncturing procedure in a human or an animal by vibrating tissue of the human or the animal in proximity to a pre-selected skin-puncturing site, the method comprising:
    providing an instrument according to claim 1;
    selecting a skin-puncturing site on the tissue;
    contacting the tissue at the selected skin-puncturing site with the tip member of the instrument;
    activating the vibration unit of the instrument to generate vibrations to vibrate the tissue, the vibrations transmitted from the vibration unit through the tip member by direct contact of the tip member with the tissue, whereby the tissue is vibrated at the skin-puncturing site; and
    puncturing the tissue with a needle at the skin-puncturing site, wherein the puncturing is carried out simultaneously with the tissue being vibrated such that vibrations transmitted into the tissue cause vibratory stimulus to nerves in proximity to the skin-puncturing site thereby minimizing pain at the skin-puncturing site.

11. The method according to claim 10, further comprising activating the lightpipe of the instrument to illuminate the skin-puncturing site.

12. The method according to claim 10, further comprising vibrating the tissue prior to puncturing the tissue or after puncturing the tissue.

13. A disposable tip for use with an instrument that includes a vibration unit and a lightpipe that is vibrated by the vibration unit, the lightpipe projecting out a forward end of the instrument, the disposable tip comprising:
    a) a tip sleeve removably mounted on the forward end of the instrument;
    b) a tip member rigidly and removably mounted on the projected end of the lightpipe, the tip member having a shape to vibrate a defined, pre-selected skin-puncturing site on a human or animal; and
    c) an elastic overmold covering the tip sleeve and the tip member, the tip sleeve including a forward portion having alternate grooves and ribs, the grooves filled by the overmold and the ribs covered by the overmold, the elastic overmold molded to a shape of the tip sleeve and the tip member and holding the tip sleeve and the tip member together, thereby separating the tip sleeve from the tip member and allowing the tip member to vibrate relative to the tip sleeve and allowing light from the lightpipe to illuminate a defined, pre-selected skin-puncturing site.

14. The disposable tip according to claim 13, wherein the tip sleeve and the tip member are spaced apart to form an annular space therebetween, and wherein the overmold fills the annular space.

15. The disposable tip according to claim 13, wherein the tip member further comprises a cup and an integrally-formed, longitudinal-extending forward portion having a free end, and wherein the overmold covers the forward portion and the forward portion defines in part at least one retraction surface.

16. The disposable tip according to claim 15, wherein the overmold covers the free end of the forward portion formed as a bulb shape.

17. The disposable tip according to claim 15, further comprising at least one longitudinal groove formed in a wider portion of the overmold.

18. The disposable tip according to claim 13, wherein the elastic overmold is composed of rubber or a thermoplastic elastomer.

19. A method for minimizing pain associated with a skin-puncturing procedure in a human or an animal by vibrating tissue of the human or the animal in proximity to a pre-selected skin-puncturing site, the method comprising:
    providing an instrument having the disposable tip according to claim 13;
    selecting a skin-puncturing site on the tissue;

contacting the tissue at the selected skin-puncturing site with the tip member of the instrument;

activating the vibration unit of the instrument to generate vibrations to vibrate the tissue, the vibrations transmitted from the vibration unit through the tip member by direct contact of the tip member with the tissue, whereby the tissue is vibrated at the skin-puncturing site; and puncturing the tissue with a needle at the skin-puncturing site, wherein the puncturing is carried out simultaneously with the tissue being vibrated such that vibrations transmitted into the tissue cause vibratory stimulus to nerves in proximity to the skin-puncturing site thereby minimizing pain at the skin-puncturing site.

20. The method according to claim 19, further comprising activating the lightpipe of the instrument to illuminate the skin-puncturing site.

21. The method according to claim 19, further comprising vibrating the tissue prior to puncturing the tissue or after puncturing the tissue.

* * * * *